United States Patent
Avila Bernal et al.

(10) Patent No.: US 12,263,030 B2
(45) Date of Patent: Apr. 1, 2025

(54) CALIBRATION AND DIAGNOSTIC PHANTOM

(71) Applicant: UNIVERSIDAD DE LOS ANDES, Bogota (CO)

(72) Inventors: Carlos Avila Bernal, Bogota (CO); Juan Sebastian Calderon Garcia, Bogota (CO); Gerardo Alfonso Roque Romero, Bogota (CO)

(73) Assignee: UNIVERSIDAD DE LOS ANDES, Bogota (CO)

( * ) Notice: Subject to any disclaimer, the term of this patent is extended or adjusted under 35 U.S.C. 154(b) by 318 days.

(21) Appl. No.: 17/599,941

(22) PCT Filed: May 22, 2020

(86) PCT No.: PCT/IB2020/054902
§ 371 (c)(1),
(2) Date: Sep. 29, 2021

(87) PCT Pub. No.: WO2020/240387
PCT Pub. Date: Dec. 3, 2020

(65) Prior Publication Data
US 2022/0192620 A1    Jun. 23, 2022

(30) Foreign Application Priority Data

May 24, 2019 (CO) .................. NC2019/0005450

(51) Int. Cl.
*A61B 6/03* (2006.01)
*A61B 6/58* (2024.01)

(52) U.S. Cl.
CPC ............... *A61B 6/583* (2013.01); *A61B 6/03* (2013.01)

(58) Field of Classification Search
CPC .......... A61B 6/583; A61B 6/03; A61B 6/502; G06T 7/00; G09B 23/28
See application file for complete search history.

(56) References Cited

U.S. PATENT DOCUMENTS 5,544,238 A * 8/1996 Galkin ................ G03D 13/007
378/207
6,570,955 B1 * 5/2003 Siffert .................... G01N 23/04
378/207

(Continued)

FOREIGN PATENT DOCUMENTS

CN    203647368        6/2014
CN    107348968 A      11/2017

(Continued)

OTHER PUBLICATIONS

Tissue Equivalent Phantom for Mammography, published 2013. Retrieved from google.com (https://www.cirsinc.com/wp-content/uploads/2019/06/011A-DS-061919.pdf) (Year: 2013).*

(Continued)

*Primary Examiner* — Dani Fox
*Assistant Examiner* — Fani Polyzos Boosalis
(74) *Attorney, Agent, or Firm* — LUCAS & MERCANTI, LLP

(57) ABSTRACT

A calibration phantom and diagnostic guide, which is composed of layers A, B, C, and D, which simulate body tissue and allow generating diagnostic guide images and/or calibration of medical equipment.

13 Claims, 5 Drawing Sheets

(56) References Cited

U.S. PATENT DOCUMENTS

| | | | | |
|---|---|---|---|---|
| 10,646,195 | B2* | 5/2020 | Jhao | A61B 6/44 |
| 2015/0178916 | A1* | 6/2015 | Sakaguchi | A61B 6/5258 |
| | | | | 378/207 |
| 2015/0305705 | A1* | 10/2015 | Goodenough | A61B 6/583 |
| | | | | 378/207 |
| 2016/0051219 | A1* | 2/2016 | Shimada | A61B 6/502 |
| | | | | 378/207 |
| 2016/0314570 | A1 | 10/2016 | Goodenough et al. | |
| 2017/0332992 | A1* | 11/2017 | Liphardt | A61B 6/502 |
| 2018/0005401 | A1 | 1/2018 | Mallozzi et al. | |
| 2020/0015772 | A1* | 1/2020 | Roeske | A61B 6/505 |
| 2022/0401057 | A1* | 12/2022 | Wu | A61B 6/583 |
| 2023/0036916 | A1* | 2/2023 | Stringer, III | A61B 6/583 |

FOREIGN PATENT DOCUMENTS

| | | |
|---|---|---|
| WO | 2015164089 A1 | 10/2015 |
| WO | 2016138449 A1 | 9/2016 |

OTHER PUBLICATIONS

Written Opinion for PCT/IB2020/054902 dated Sep. 4, 2020.
P. Kinahan, et al; Simultaneous estimation of bias and resolution in PET images with a long-lived pocket phantom system; Tomography; vol. 4; No. 1; Mar. 2018; pp. 33-41.
International Search Report for PCT/IB2020/054902 dated Sep. 4, 2020 with English translation.

* cited by examiner

CALIBRATION AND DIAGNOSTIC PHANTOM

CROSS REFERENCE TO RELATED APPLICATION

This Application is a 371 of PCT/IB2020/054902 filed on May 22, 2020, which claims priority of Colombian Application No. NC2019/0005450 filed May 24, 2019, each of which are incorporated herein by reference.

FIELD OF INVENTION

The present invention relates to the area of calibration of imaging equipment for medical diagnosis and, more specifically, to a phantom that allows calibration of equipment intended for imaging diagnosis by generating quality images and providing a guide on diseases in this technical field.

BACKGROUND OF THE INVENTION

In the prior art, there were phantoms with two-dimensional distributions of inlays designed to calibrate medical equipment. Among these, we can find the CIRS011 and CIRS015 phantoms, which account for mammography equipment's performance. However, both devices have the disadvantage of not portraying real objects since their materials (aluminum trioxide or calcium carbonate) are not the same as those found in the human body. Likewise, the spatial distributions of the inlays are all aligned in the same plane (2D), an atypical situation in real diagnostic images, where it is always possible to observe a three-dimensional distribution of the lesions found in the tissue.

Similarly, a phantom has been developed to perform image reconstruction verification using the digital tomosynthesis technique (Patent No. WO 2014/041469 A1, "Mammographic Tomography Test Phantom"). This device is exclusively for the calibration of mammographic equipment, so it also does not portray morphologies that simulate real pathologies in patients.

As in the previous case, there are more instances in which the development of phantoms has focused exclusively on the calibration of diagnostic equipment. The Tomophan TSP004 device, developed by the company The Phantom Laboratory, was designed with inlays in three-dimensional distribution, with inlay sizes on the order of hundreds of micrometers. The design is built specifically for equipment calibration, and its size occupies a substantial area of any commercial equipment detector.

In both cases presented above, no devices are provided for direct aid in diagnosing breast disease.

In addition to the above calibration phantoms, there are test phantoms. One of these cases is developing a device for calibration of panoramic X-ray equipment for dentistry, with three-dimensional distributions of the absorbing elements (Patent No. U.S. Pat. No. 5,083,920A, "Phantom For A Dental Panoramic X-Ray Apparatus"). This device must be placed directly where the patient is positioned and is designed to verify the operating status of the panoramic equipment, in particular, the absorption and rotational movement of the source-detector array. However, given its design, it is not possible to use it in conjunction with a patient, and it is made of materials that do not simulate diseases. Finally, the images of a panoramic dental unit are intended to show in one plane a three-dimensional structure such as the human teeth, following its curvature, thus removing any three-dimensional information found in the sample.

In view of the foregoing, there is a need for a phantom, which can be used during medical imaging and provide a disease diagnostic guide while at the same time providing calibration information of the imaging equipment.

The present invention provides a solution to the said problem by means of a phantom comprising modules with inlays (200), a calibrator object (122), and an absorption matrix (101), which together provide images of disease diagnosis guide, at the same they can provide information of the conditions of medical equipment.

BRIEF DESCRIPTION OF THE INVENTION

The present invention is about a calibration phantom and diagnostic guide (100), which is located in the free intake space (301) of medical X-ray diagnostic imaging equipment and provides images for calibration and/or diagnostic guide.

The phantom (100) comprises inlay modules (200), a calibrator object (122), and an absorption matrix (101), which together provide diagnostic guidance images of diseases while at the same time can provide information on the conditions of medical equipment.

For radiological physicians, the phantom, according to the invention, allows them to have, under the same operating conditions during X-ray acquisition, an image of the organ (302) together with the image of the reference pattern delivered by the phantom (100). This gives the advantage of directly referencing the diagnostic patterns with those characteristics found in the patient's tissue.

As for the technicians who calibrate the medical equipment, they can see the evolution of the performance of the equipment, shot by shot over time, as the phantom (100) is used. Likewise, they can quickly discard images if any image anomaly is observed in the phantom (100) patterns or a reduction in contrast or image quality that needs to be corrected. By having a direct and continuous evaluation, there is potential to save equipment usage in independent calibration activities. It is possible to perform an evaluation of the image quality, using the image region where the phantom (100) appears, to calculate the Mean Transfer Function MTF of the system, and then apply the necessary corrections to improve the quality of the following images.

According to the patients, once they receive the image, it can have a guide for interpretation of the results by having a direct reference to a standard diagnosis. That effectively allows for comparative studies of patients' actual organ (302) against the phantom (100) in the same image. To achieve high overall diagnostic effectiveness, the phantom (100) can have inlay modules (200) that simulate cases of the disease, as well as possible examples of healthy structural formations.

For calibration and research activities, having direct comparisons between images of the phantom (100) along with real tissue, healthy or diseased, can contribute to improvements in diagnosis, evaluation, and subsequent studies, not to mention allowing for the creation of a comparative database of real cases along with reference cases, ensuring the best possible use of the images, in terms of Carrier-to-Noise Ratio (CNR)/Signal-to-Noise Ratio (SNR), disease morphologies, resolution of the equipment used, and dose. Using the same reference pattern for multiple X-ray images allows a better interpretation of the information at the medical and research levels. The phantom (100) allows establishing a measurement scale of X-ray absorption in the image, allowing setting sizes of the morphologies found. In turn, it also makes it possible to quickly determine the geometric magnification at which the image was obtained.

That is also a research aid, as it helps in an accurate and repeatable interpretation of the images taken.

DESCRIPTION OF THE DRAWINGS

FIG. 7A: Top view of the inlaid module (200), wherein the inlays are diagnostic inlays.

FIG. 7B: Top view of the inlaid module (200), wherein the inlays are calibration inlays.

DETAILED DESCRIPTION OF THE INVENTION

Figure 1:
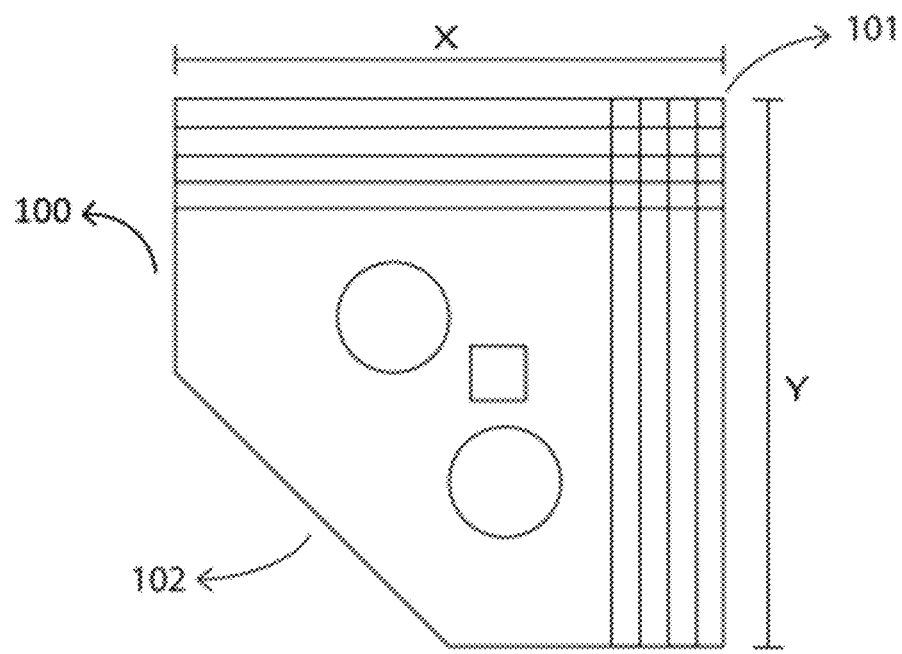
FIG. 1: Top view of the phantom (100) according to the present invention.
Figure 2:
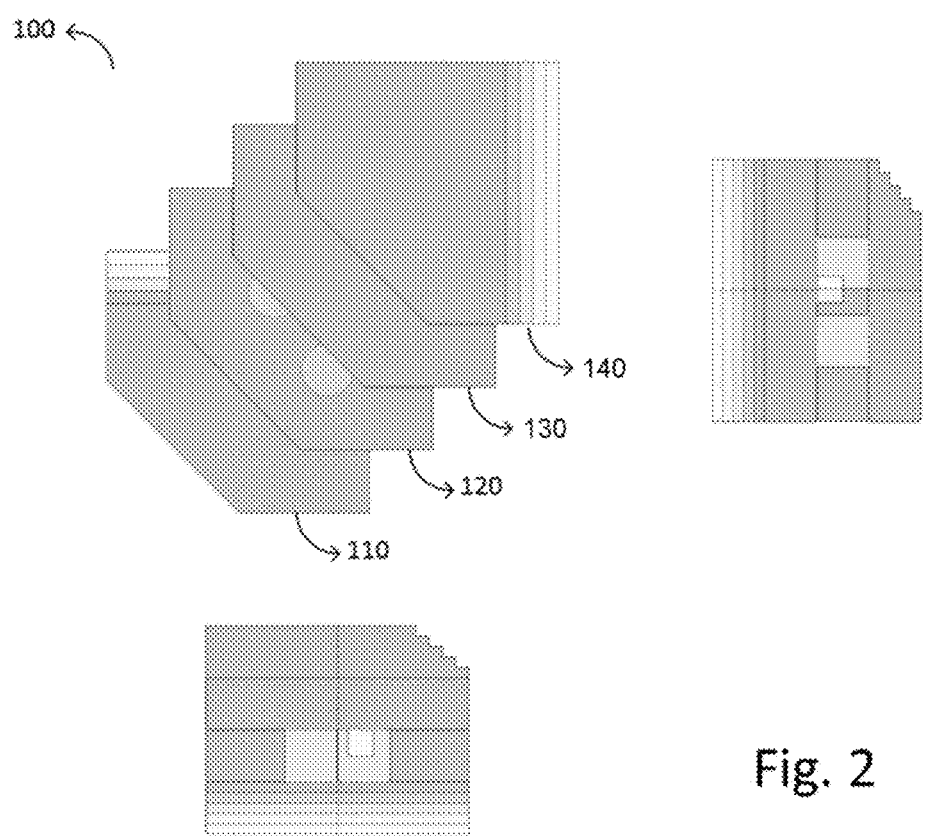
FIG. 2: Top, side, and front view of the phantom (100), wherein the top view expands into layers A (110), B (120), C (130), and D (140), which compounds the phantom (100).

As shown in FIGS. 1 and 2, the present invention relates to a calibration phantom and diagnostic guide (100), which is composed of layers A (110), B (120), C (130), and D (140), which simulate body tissue and allow generating diagnostic guide images and/or calibration of medical equipment.

Regarding the dimensions of the phantom (100), it has a height between 3 cm and 7 cm, preferably 4 cm. The phantom (100) has a width X and a length Y of between 4 cm and 10 cm, preferably 5 cm.

In possible embodiments of the phantom (100), its cross-sectional shape in the XY plane may vary depending on the medical equipment and the organ on which the diagnostic image is taken. This shape may be regular, such as a circle, rectangle, or polyhedron, or irregular.

In possible embodiments of the phantom (100), layers A (110), B (120), C (130), and D (140) may be integrated into a solid object or could be modular and interchangeable with each other.

In one possible embodiment, the phantom (100) may have a diagonal (102) (as shown in FIG. 1), which facilitates placement of the phantom (100) in the acquisition area (300) next to the organ (302) on which medical imaging is desired.

In a preferred embodiment, the phantom (100) is a mammographic phantom; however, it can be used in other types of X-ray diagnostic imaging. Illustrative but not restrictive examples are kidney imaging, dental imaging, urinary tract imaging, among others.

Figure 3:
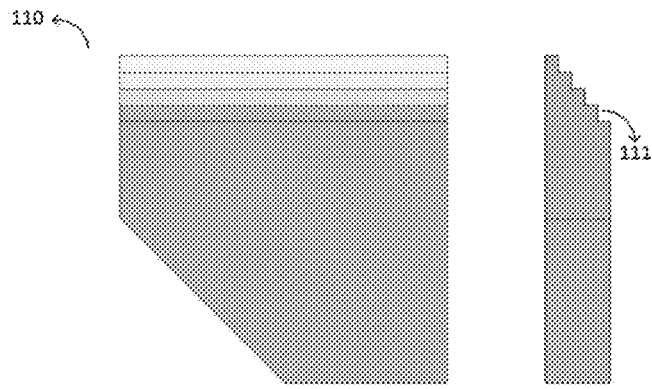
FIG. 3: Top, side, and front view of layer A (110) of the phantom (100).

According to FIG. 3, layer A (110)a is characterized in that it comprises steps (111), which are located on one of the sides of the X-axis of the phantom (100). Preferably the steps (111) range between 2 and 10 steps, and more preferably, the steps are 4 steps.

In a preferred embodiment of the phantom (100), each of the steps (111) has a different height therebetween.

The preferred height of layer A (110) is 1 cm. The material of which it is composed is selected to simulate human tissue and is selected from the category of thermoset plastics, preferably polymethylmethacrylate (PMMA).

Figure 4:
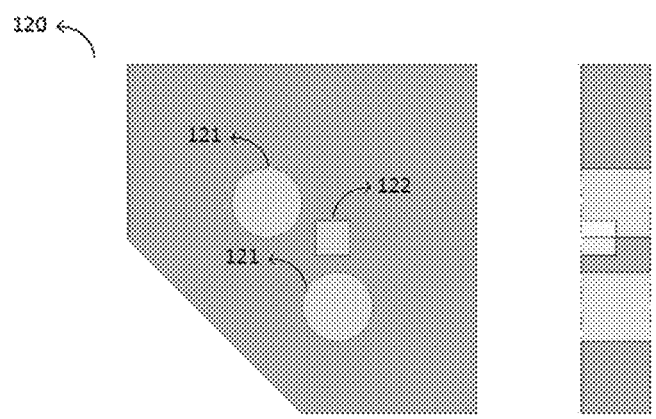
FIG. 4: Top, side, and front view of layer B (120) of the phantom (100).

According to FIG. 4, layer B (120) is characterized in that it comprises one or more holes (121) and one or more calibration objects (122). The holes (121) are present for locating therein the inlay modules (200). The number of holes (121) is limited by the available area resulting from the X and Y dimensions of the phantom (100).

Preferably, the holes (121) are not overlapping with steps (111) nor (141), neither with the calibration object (122).

The calibration object (122) is characterized in that it has at least one straight side, which enables the recognition of the resolution of the imaging equipment. The calibration object (122) may be in the form of a sheet, wire, or other shapes. The material of the calibration object (122) may be any metal, preferably aluminum.

The preferred height of layer A (120) is 1 cm. Its material is selected to simulate human tissue and is selected from the category of thermoset plastics, preferably polymethylmethacrylate (PMMA).

Figure 5:
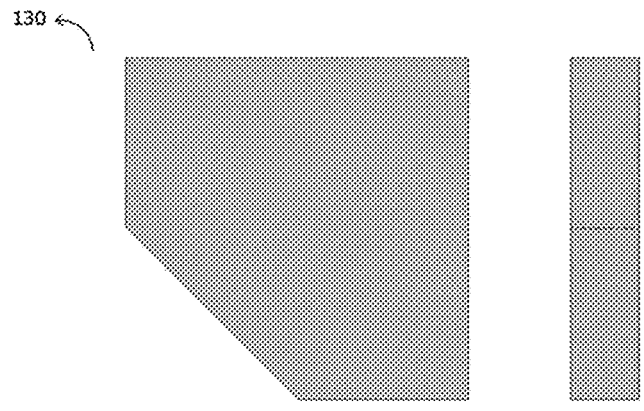
FIG. 5: Top, side, and front view of layer C (130) of the phantom (100).

According to FIG. 5, layer C (130) is characterized in that it has a variable height between 0 cm and 7 cm. Its functionality provides radiation absorption variability that simulates organs of different sizes and tissue type ratios (e.g., higher or lower ratio of muscle tissue, breast tissue, and adipose tissue).

The material of layer C (130) may be selected from a thermoset plastic, preferably polymethylmethacrylate (PMMA), or a wax, preferably paraffin wax).

Figure 6:
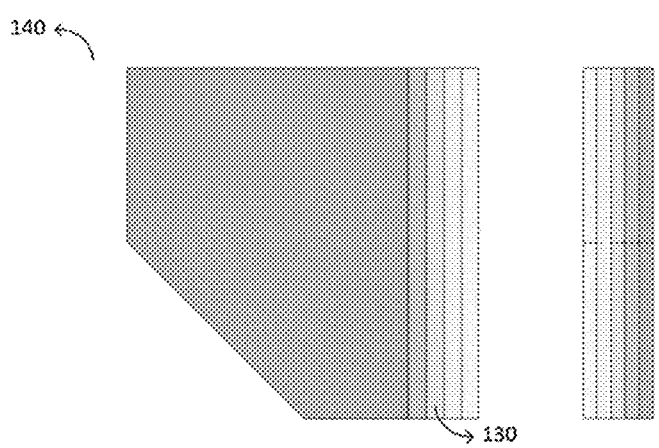
FIG. 6: Top, side, and front view of layer D (140) of the phantom (100).

According to FIG. 6, layer D (140) is characterized in that it comprises steps (141), which are located on one of the sides of the Y-axis of the phantom (100). Preferably the steps (111) range between 2 and 10 steps, and more preferably, the steps are 4 steps.

In a preferred embodiment of the phantom (100), each of the steps (141) has different height from each other and is also different from the steps (111).

The preferred height of layer D (140) is 1 cm. The material of which it is composed is selected to simulate human tissue and is selected from the category of thermoset plastics, preferably polymethylmethacrylate (PMMA).

Figure 8:
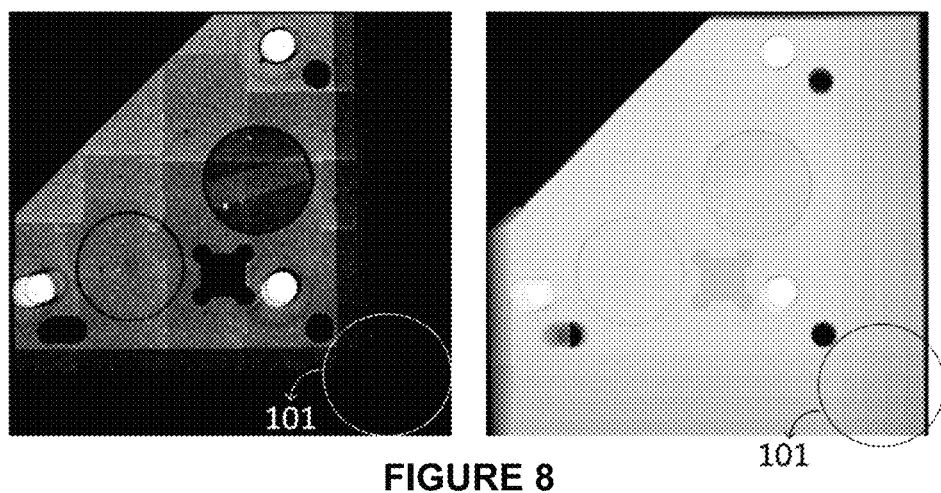
FIG. 8: Obtained images by exposing the phantom (100) to two radiation levels, wherein the absorption matrix formation is evidenced.

The overlapping of the steps (111) and (141) from the top view of the phantom (100) gives the configuration of the matrix (101) (as shown in FIGS. 8 and 1), which simulates how the sample tissue shown in the image, changes its absorption due to morphological characteristics, by means of a change in thickness of a single reference material.

In one possible embodiment of the invention, the steps (111) and (141) are in the same layer of the phantom (100).

Figure 10:
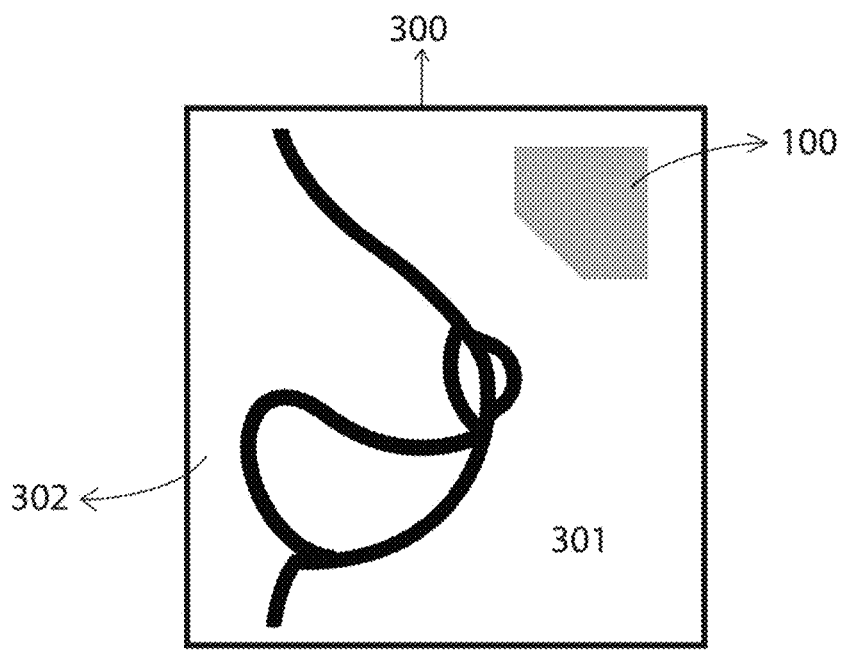
FIG. 10: Representation of spatial location of an organ (302) and the phantom (100) in an acquisition space (300) when performing a diagnostic X-ray image acquisition, wherein it is evident that the phantom (100) is located in the free acquisition space (301). In the figure, a breast is represented as an organ (302) during mammography.

As illustrated in FIG. 10, the absorption matrix replicates the radiation intensity of different regions of the sample. Given the specific imaging conditions of imaging, in which the organ (302) is compressed to remain static, changes in intensity can only be observed due to changes in its radiation absorption features, not thickness. Thus, the phantom (100) allows for calibration between different material attenuation coefficients, depending on the proportion of tissue present in each region, and the thicknesses of a single calibration material with well-known attenuation characteristics, without changing the overall height of the phantom (101).

Figure 7:
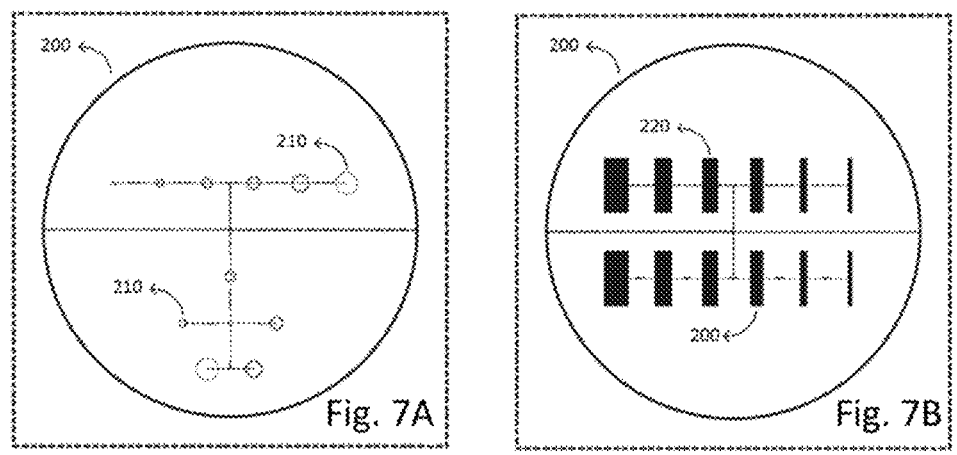
FIG. 7: Top view of the inlaid module (200).
Figure 9:
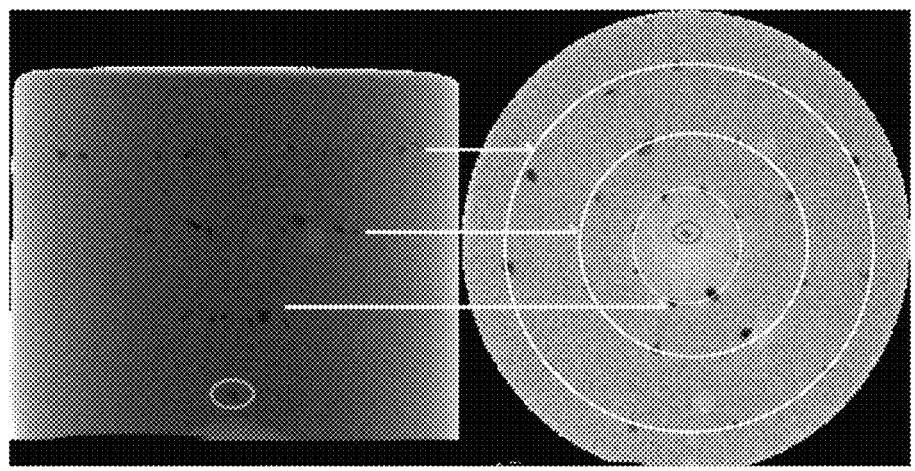
FIG. 9: Top and lateral view of the inlaid module (200), wherein the inlays are diagnostic inlays with a 3D-geometric distribution.

As shown in FIG. 7, the modules with inlays (200) have a diameter ranging from 10 mm to 20 mm, preferably 10 mm, and height equal to the layer in which they are contained [layer B (120)]. Their material is the same as the layer in which they are contained [layer B (120)]. Preferably, the inlays have a 3D distribution, as illustrated in FIG. 9.

The inlay modules (200) may have two types of inlays, diagnostic inlays (210) or calibration inlays (220), in accordance with the illustrated in FIGS. 7A and 7B.

The diagnostic inlays (210) may have a geometric distribution, such as a linear distribution or a spiral, or pathology distributions, such as distributions provided by imaging information and data systems, preferably the Breast Imaging Reporting and Data System (BI-RADS).

Preferably, the diagnostic inlays (210) are sphere or spheroid-shaped with a size between 150 um and 800 um. Their material may be selected from calcium such as hydroxyapatite, aluminum trioxide, calcium carbonate, or metals. Preferably, the material is hydroxyapatite.

The calibration inlays (220) may have a geometric distribution, preferably a linear distribution.

Preferably, the inlays have a linear or cylindrical shape with a diameter between 150 um and 800 um, and a length between 1 mm and the size of the largest dimension of the inlaid module (200). Its material may be selected from any low absorption material to radiation, such as plastic, preferably nylon.

As can be determined by a person skilled in the art, there are possible variations as to the dimensions, or materials, and components of the invention that would accomplish the same purpose according to the needs of the technical field.

The invention claimed is:

1. A phantom that simulates body tissue comprising diagnostic guide elements for diagnostic imaging for medical diagnosis purposes and medical calibration elements for calibrating the medical equipment,
   wherein the diagnostic guide elements and medical calibration elements are a combination of the following layers:
   layer A comprising steps which are located on one side of an X-axis of the phantom, wherein the steps are diagnostic guide elements;
   layer B comprising one or more holes and one or more calibrator, wherein the one or more holes comprises inlaid modules comprising diagnostic guide elements or medical calibration elements;
   layer C being of variable height to provide radiation absorption variability that simulates organs of different sizes and tissue type ratios;
   layer D comprising steps which are located on one side of a Y-axis of the phantom, wherein the steps are diagnostic guide elements.

2. The phantom according to claim 1, wherein the steps of layer A and layer D are overlapping from a top view of the phantom providing a configuration of a matrix.

3. The phantom that simulates body tissue according to claim 2, wherein the matrix replicates radiation intensity of different regions of a tissue sample without changing an overall height of the phantom.

4. The phantom according to claim 1, wherein the calibrator has at least one straight side.

5. The phantom according to claim 1, wherein the phantom composed of layers A, B, C, and D in total have a height between 3 cm and 7 cm.

6. The phantom that simulates body tissue according to claim 1, wherein the inlaid modules, have a diameter between 10 mm and 20 mm.

7. The phantom that simulates body tissue according to claim 6, wherein the inlaid modules comprises inlays having a 3D distribution, wherein the inlays are diagnostic inlays or calibration inlays.

8. The phantom that simulates body tissue according to claim 1, wherein the layers A, B, C, and D are integrated into a solid object, or arranged in a modular and interchangeable configuration between the layers.

9. The phantom that simulates body tissue according to claim 1, wherein the phantom has a diagonal side which facilitates placement of the phantom in an acquisition area next to a body part on which medical imaging is desired.

10. The phantom that simulates body tissue according to claim 1, wherein layer A and layer D are each composed of a material that simulate human tissue.

11. The phantom that simulates body tissue according to claim 1, wherein layer C is composed of a thermoset plastic or a wax.

12. The phantom that simulates body tissue according to claim 1, wherein each of the steps of layer A and layer D has a different height from each other.

13. A phantom that simulates body tissue comprising diagnostic guide elements for medical diagnosis purposes imaging and calibration elements for calibrating the medical equipment, wherein the phantom further comprises steps which are located on one side of an X-axis of the phantom, and steps which are located on one side of a Y-axis of the phantom, wherein the steps are overlapping and from a top view of the phantom gives a configuration of a matrix, and
   wherein the steps are made of a single material with a specific x-ray attenuation coefficient.

* * * * *